United States Patent
Zaman et al.

(10) Patent No.: US 8,284,208 B2
(45) Date of Patent: Oct. 9, 2012

(54) PROCESSES AND APPARATUS FOR INFORMATION TRANSFER

(75) Inventors: Sabih Qamaruz Zaman, Elm Grove, WI (US); Jon Charles Omernick, Wauwatosa, WI (US); Stephanie Allison Swenor, Mukwonago, WI (US)

(73) Assignee: General Electric Company, Schenectady, NY (US)

( * ) Notice: Subject to any disclaimer, the term of this patent is extended or adjusted under 35 U.S.C. 154(b) by 923 days.

(21) Appl. No.: 11/439,920

(22) Filed: May 24, 2006

(65) Prior Publication Data

US 2007/0273697 A1  Nov. 29, 2007

(51) Int. Cl.
*G06F 13/14* (2006.01)
(52) U.S. Cl. ............... 345/520; 378/21; 378/62; 378/98; 382/131; 382/132
(58) Field of Classification Search .................. 345/520; 378/21, 62, 98; 382/131, 132
See application file for complete search history.

(56) References Cited

U.S. PATENT DOCUMENTS

| | | | |
|---|---|---|---|
| 5,077,768 A | | 12/1991 | Shigyo et al. |
| 5,165,100 A * | | 11/1992 | Hsieh et al. ................... 382/131 |
| 5,225,980 A * | | 7/1993 | Hsieh et al. ..................... 378/18 |
| 5,351,047 A * | | 9/1994 | Behlen ............................. 341/67 |
| 5,414,648 A * | | 5/1995 | Morgan et al. ................ 702/155 |
| 5,592,524 A * | | 1/1997 | Roper et al. ................. 378/98.2 |
| 5,630,101 A * | | 5/1997 | Sieffert .......................... 710/11 |
| 5,729,584 A * | | 3/1998 | Moorman et al. ............ 378/146 |
| 5,740,801 A * | | 4/1998 | Branson ......................... 600/407 |
| 5,870,051 A * | | 2/1999 | Warburton et al. ........... 341/155 |
| 6,205,199 B1 * | | 3/2001 | Polichar et al. .............. 378/98.8 |
| 6,289,115 B1 * | | 9/2001 | Takeo ............................ 382/130 |
| 6,370,217 B1 | | 4/2002 | Hu et al. |
| 6,397,098 B1 * | | 5/2002 | Uber et al. .................... 600/431 |
| 6,448,544 B1 * | | 9/2002 | Stanton et al. ............. 250/208.1 |
| 6,542,575 B1 * | | 4/2003 | Schubert et al. ............. 378/98.4 |
| 6,768,784 B1 * | | 7/2004 | Green et al. ..................... 378/62 |
| 7,155,546 B2 * | | 12/2006 | Seto .............................. 710/100 |
| 7,171,509 B2 * | | 1/2007 | Cassidy ........................ 710/308 |
| 7,231,641 B2 * | | 6/2007 | Wijnstra ....................... 719/316 |
| 7,281,246 B1 * | | 10/2007 | Rapakko et al. .............. 717/175 |
| 7,505,554 B2 * | | 3/2009 | Ting ................................ 378/19 |
| 2001/0048734 A1 * | | 12/2001 | Uppaluri et al. .............. 378/207 |
| 2002/0085672 A1 * | | 7/2002 | Ganin et al. .................. 378/108 |
| 2002/0101527 A1 * | | 8/2002 | Endo ............................. 348/302 |

(Continued)

FOREIGN PATENT DOCUMENTS

WO  WO 01/33921 A1 * 5/2001

*Primary Examiner* — Daniel Washburn
(74) *Attorney, Agent, or Firm* — William Baxter; Michael Smith, Esq.

(57) ABSTRACT

Systems, processes and apparatus are described through which signals are modified within a system. A signal conditioning module is configured for insertion into the system and provides capability for expansion of information exchange capabilities between system elements responsive to modification of the system. The signal conditioning module includes a first link for supplying coordinated information to multiple display elements to synchronize information displayed by each of the multiple display elements, a second link for supplying coordinating data internal to a control system for a nondestructive imaging system to synchronize the internal data with the information displayed by each of the multiple elements and a third link for supplying coordination descriptions relevant to a nondestructive imaging task performed by the system to a memory, including an image and data relevant to that image.

16 Claims, 8 Drawing Sheets

U.S. PATENT DOCUMENTS

| | | | |
|---|---|---|---|
| 2002/0154802 A1* | 10/2002 | Goldkuhl et al. | 382/132 |
| 2003/0058998 A1* | 3/2003 | Aufrichtig et al. | 378/207 |
| 2004/0086077 A1* | 5/2004 | Moriyama | 378/29 |
| 2004/0128204 A1* | 7/2004 | Cihla et al. | 705/26 |
| 2004/0162775 A1* | 8/2004 | Winklevoss et al. | 705/36 |
| 2004/0179651 A1* | 9/2004 | Tong et al. | 378/98.8 |
| 2004/0230504 A1* | 11/2004 | Katada et al. | 705/29 |
| 2004/0234032 A1* | 11/2004 | Nokita | 378/98.8 |
| 2004/0247167 A1* | 12/2004 | Bueno et al. | 382/132 |
| 2005/0110788 A1 | 5/2005 | Turner et al. | |
| 2005/0135564 A1* | 6/2005 | Dippl et al. | 378/167 |
| 2005/0159903 A1 | 7/2005 | Ogura | |
| 2005/0203389 A1* | 9/2005 | Williams | 600/431 |
| 2007/0140428 A1* | 6/2007 | Toth | 378/108 |
| 2007/0153980 A1* | 7/2007 | Butzine et al. | 378/198 |
| 2007/0202836 A1* | 8/2007 | Zaman et al. | 455/343.2 |
| 2007/0226258 A1* | 9/2007 | Lambdin et al. | 707/104.1 |
| 2009/0214094 A1* | 8/2009 | Williams et al. | 382/131 |

* cited by examiner

PROCESSES AND APPARATUS FOR INFORMATION TRANSFER

FIELD OF THE DISCLOSURE

This disclosure relates generally to augmenting or expanding capabilities of existing systems, notably in conjunction with additional modules, in particular to expansion of information exchange capabilities between system elements responsive to modifications of existing systems, and more particularly, to techniques for facilitating such in a context of mobile nondestructive evaluation tools, including tools employed in medical diagnosis.

BACKGROUND

Many medical diagnoses rely on non-invasive diagnostic tools to provide information, often in the form of images, descriptive of status of internal portions or organs of a patient. These tools include thermal imaging (e.g., mammography), ultrasonic probes, magnetic resonance imaging techniques, positron emission tomography, computed tomography (CT), single photon emission-computed tomography (SPECT) and optical imaging and/or X-ray radiation based techniques. In some minimally invasive instances, imaging aids, such as contrast-enhancing agents, are introduced into the subject or patient to aid in increasing available data content from the non-destructive imaging technique or techniques being employed.

Each of these tools presents advantages in particularized situations, has technological limitations, may require set-up and analysis time, can include risks and also has associated costs. As a result, a cost-benefit analysis that also reflects the degree of urgency with respect to a particular diagnostic trajectory often favors usage of X-ray radiation-based measurement techniques.

However, exposure to X-ray radiation can result in some risk to the test subject or patient. For at least this reason, the dosage of X-ray radiation incident on the patient, organ or object being evaluated/imaged, is often carefully chosen and controlled, for example, variables such as a current-time product (milliAmpere-seconds or mAs) of current to the X-ray tube (mA or milliAmperes) multiplied by exposure time (seconds), peak voltage applied to the X-ray tube (kVp or kiloVolts peak), and by selecting and defining an area to be exposed to provide successful imaging via masking, based on the task and the test subject or patient's parameters, with least health risk to the patient or radiation exposure to the object being imaged. The Food and Drug Administration has recently identified X-ray radiation as potentially having carcinogenic effects, adding impetus to the desire to reduce overall exposure while still providing imaging characteristics capable of enabling rapid, effective and accurate diagnostic aids.

Several factors influence image quality resulting from an X-ray radiation procedure. Statistical photon noise resulting from characteristics of the X-ray radiation source and the X-ray radiation generation conditions tends to dominate other noise sources in formation of an X-ray radiation-based image. Signal conditioning consistent with achieving suitable contrast between various image portions, and contrast enhancement techniques, are also important considerations in providing diagnostic images, and these issues require increasingly sophisticated treatment as dose and/or photon energy are decreased.

One of the key tenets of medical X-ray radiation imaging is that image quality should be carefully considered in determining exposure conditions. Exposure considerations include predetermined dose criteria vis-a-vis dose of X-ray radiation delivered to the test subject or patient in order to provide images. The design and operation of a detector used for medical X-ray radiation imaging should therefore be tailored, responsive to the particularized task and measurement conditions, including variables in test subject mass, opacity and the like, to provide high image quality for each X-ray radiation exposure that is incident on the detector. However, diagnostic medical tools such as X-ray radiation-based imaging systems are precision instruments, very carefully designed, and then built to exacting standards. As such, these kinds of imaging systems represent significant capital investments. Additionally, training personnel to maintain and calibrate such equipment, to operate and then to interpret data obtained via these diagnostic tools also encompasses additional investment. Also, comparison of data from one assessment to another, and from one timeframe to another, is greatly facilitated when the data are collected and processed in a relatively well-understood and documented context. At the same time, technical developments may provide opportunity to leverage existing infrastructural elements by retrofitting them using sophisticated, newly-developed technological subsystems, and this also may facilitate capabilities not present in the ensemble of system elements contemplated at initial design and deployment.

For example, X-ray radiation systems and other non-destructive and largely non-invasive characterization devices have realized dramatic changes in capability during the last century or more. Medical diagnostic capabilities unimaginable prior to C. W. Roentgen's observations of X-ray radiation images in 1895 have fostered intense and remarkably fruitful research, study and development, improving medical treatment capabilities to such an extent as to have, in turn, played pivotal roles leading to conception and subsequent maturation of entirely new medical specialties and treatment options.

One new tool resulting from this research employs pixelated X-ray radiation detectors (detectors comprising a geometric array of multiple detector elements, where each detector element may be individually representative of at least a portion of a picture element or pixel in the resultant image). These detectors are increasingly being employed, particularly for medical imaging. Among other things, they facilitate digital representation of images and other data resulting from usage of the systems, which, in turn, enables digital signal processing, data storage and data transmission technologies.

A significant result of these technological innovations is that the potential and capability for real-time consultation between multiple experts, such as medical doctors, during what is called the "golden hour" following a medically-significant event, is greatly enhanced. Representation of such information in digital formats eases transmission, reception and standardized display of the information without incurring loss of acuity of data obtained from the measurement process and greatly eases reduction of noise from the transmission/reception process. In turn, this facilitates capability for multiple experts to collaborate virtually instantly, even from geographically diverse locations, despite extreme scenarios, e.g., triage following an unanticipated disaster. As a result, these capabilities represent strong impetus to incorporate new subsystems within existing diagnostic instruments.

However, incorporation of embodiments of such subsystems may result in some types of incompatibilities within the systems themselves. Aspects of system performance other than those bearing directly on factors motivating addition of modules incorporating recent advances can then have somewhat subtle, and unforeseen, impact on overall system performance, operation and maintenance issues.

For the reasons stated above, and for other reasons discussed below, which will become apparent to those skilled in the art upon reading and understanding the present disclosure, there are needs in the art to provide modified system input/output and/or maintenance information in support of increasingly stringent and exacting performance and economic standards in settings such as medical instrumentation.

SUMMARY

The above-mentioned shortcomings, disadvantages and problems are addressed herein, which will be understood by reading and studying the following disclosure.

In one aspect, a signal conditioning module configured for insertion into a system is disclosed. The signal conditioning module provides capability for expansion of information exchange capabilities between system elements responsive to modification of the system. The signal conditioning module includes a first link for supplying coordinated information to multiple display elements to synchronize information displayed by each of the multiple display elements, a second link for supplying coordinating data internal to a control system for a nondestructive imaging system to synchronize the internal data with the information displayed by each of the multiple elements and a third link for supplying coordination descriptions relevant to a nondestructive imaging task performed by the system to a memory, including an image and data relevant to that image.

In another aspect, a process for signal conditioning operative in the context of a nondestructive imaging system includes an act of conditioning signals exchanged between a display and control module, at least one operator console and a processor via a signal conditioning module inserted between the display and control module and other elements of the imaging system. The act of conditioning includes coordinating values selected via either the display and control module or the operator console with analogous values associated with other system elements. The process also includes an act of storing the coordinated values in a memory. The stored coordinated values are linked to an image formed with the imaging system using at least some of the coordinated values as control parameters.

In a yet another aspect, an article of manufacture comprises a computer-readable medium embodying computer code that includes computer-readable instructions, which, when executed by one or more processors, causes the one or more processors to modify signal exchange capabilities of a signal conditioning module in an X-ray radiation system responsive to revision of one or more elements in the X-ray radiation system. The signal conditioning module is coupled between at least one display and control module, at least one operator console and at least one system controller. The instructions also cause the one or more processors to coordinate values selected via at least one of the display and control module, the operator console and the system controller with analogous values in at least one other of the display and control module, the operator console and the system controller.

Systems, clients, servers, processes, and computer-readable media of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which are shown, by way of illustration, specific embodiments which may be practiced. These embodiments are described in sufficient detail to enable those skilled in the art to practice the embodiments, and it is to be understood that other embodiments may be utilized, and that logical, mechanical, electrical and other changes may be made, without departing from the scope of the embodiments.

As used herein, the term "illumination" refers to exposure to photons, electromagnetic radiation, X-ray radiation, phonons (e.g., insonification via ultrasound) or other wave phenomena, which do not necessarily correspond to light that is visible to a human eye. Ranges of parameter values described herein are understood to include all subranges falling therewithin. The following detailed description is, therefore, not to be taken in a limiting sense.

The detailed description is divided into six sections. In the first section, a system level overview is described. In the second section, adaptive system elements are described. In the third section, embodiments of processes are described. In the fourth section, graphical user interfaces capable of utility with the system are described. In the fifth sections, hardware and an operating environment in conjunction with which embodiments may be practiced are described. In the sixth section, a conclusion of the detailed description is provided. A technical effect of the systems and processes disclosed herein includes at least one of programmably expanding capability for exchange of data and control signals in X-ray radiation systems.

I. System Overview

Figure 1:
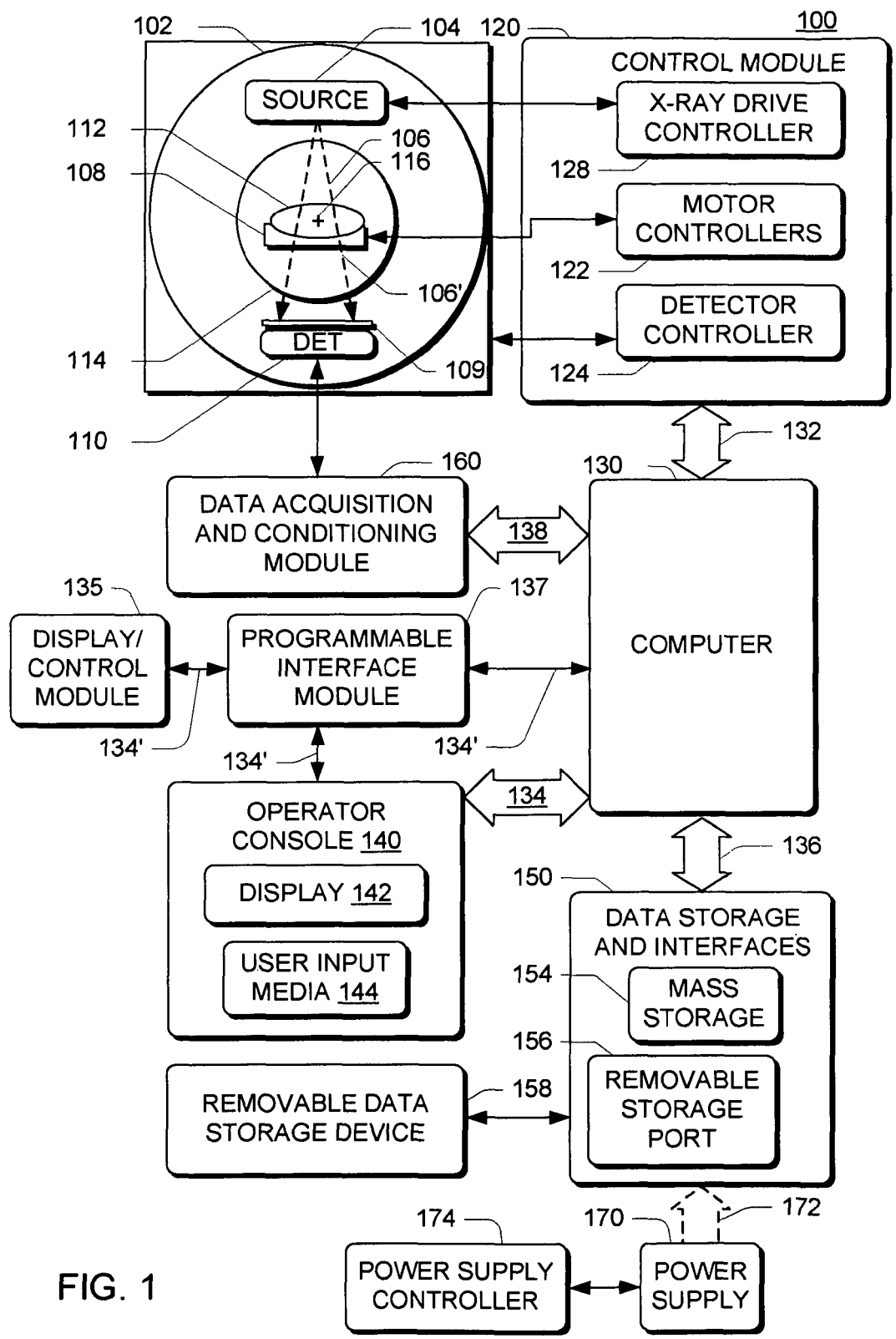
FIG. 1 is a simplified block diagram of an overview of a system configured to improve X-ray radiation imaging operations.

FIG. 1 is a simplified diagram of an overview of a modified system 100 configured to improve X-ray radiation imaging operations. In particular, the system 100 is configured to provide digitized images from non-destructive imaging systems based on X-ray radiation, while reducing the radiation dose employed, compared to conventional X-ray radiation imaging systems and processes. The system 100 optionally includes a gantry 102 or other support for an illumination source 104, such as an X-ray radiation illumination source, capable of providing illumination 106, such as X-rays or other non-destructive internal imaging illumination, and may optionally include a test subject support 108 that is transmissive with respect to the illumination 106 and that is positioned above a scintillator 109 and detector 110 that is also opposed to the illumination source 104. Alternatively, a detector 110 that is a direct conversion detector may be employed without need for a scintillator.

In one embodiment, components of the system 100 and a test subject 112 are maintained in a defined geometric relationship to one another by the gantry 102. A distance between the illumination source 104 and the detector 110 may be varied, depending on the type of examination sought, and the angle of the illumination 106 respective to the test subject 112 can be adjusted with respect to the body to be imaged responsive to the nature of imaging desired.

In one embodiment, the test subject support 108 is configured to support and/or cause controlled motion of the test subject 112, such as a living human or animal patient, or other test subject 112 suitable for non-destructive imaging, above the scintillator 109/detector 110 so that illumination 106' is incident thereon after passing through the test subject 112. In turn, information from the detector 110 describes internal aspects of the test subject 112.

The scintillator 109 may be a conventional CsI scintillator 109, optically coupled to an array of photodiodes (FIGS. 2 and 3, infra), such as a two-dimensional array of photodiodes and suitable control transistors formed using semiconductor material such as amorphous silicon, or any other form of detector 110 suitable for use with the type or types of illumination 106 being employed, such as X-ray radiation. The detector elements are typically tesselated in a mosaic. The scintillator 109 converts incident photons comprising electromagnetic radiation, such as X-ray radiation, from high-energy, high-frequency photons 106', into lower-energy, lower-frequency photons corresponding to spectral sensitivity of the detector elements, in a fashion somewhat analogous to fluorescence, as is commonly known in the context of many visible-light sources in use today. Alternatively, the detector 110 may be formed as a flat-panel array including amorphous Silicon ($\alpha$-Si) active elements, together with either a scintillator layer 109, or a direct converter material such as Cadmium Zinc Telluride (CdZnTe), Mercuric Iodide ($HgI_2$), Lead Iodide ($PbI_2$), or amorphous Selenium ($\alpha$-Se).

In some modes of operation, such as CT, the gantry 102 and test subject support or table 108 cooperatively engage to move the test subject 112 longitudinally, that is, along an axis extending into and out of the plane of FIG. 1 and within an opening 114. In some modes of operation, the gantry 102 rotates the X-ray radiation source 104 and detector 110 about an axis 116 while the support 108 moves longitudinally to provide a helical series of scans of the test subject 112, where a pitch of the helices is defined as a ratio of a longitudinal distance traveled by the table 108 during a complete revolution of the gantry 102, compared to a length of the detector 110 along the axis of linear motion.

In one embodiment, the detector 110 comprises a floating receptor, that is, the detector 110 is not coupled to a gantry and is not associated with a patient table 108. In other words, the detector 100 that is a floating digital detector is portable and is hence 'floating' with respect to other elements of the system 100, and the detector 110 that is a floating digital detector is attached to the rest of the system 100 via a tether. The term 'floating' is meant to indicate that its position is completely subject to the user and is not controlled via a gantry, table or other system device. In one embodiment, the detector 100 that is a floating digital detector may be postured opposite the source 104 with the test subject 112 being located between the source 104 and the detector 110 that is a floating digital detector, by placing the detector 110 beneath the test subject 112, for example.

The system 100 also optionally includes a control module or controller 120. The controller 120 may include a motor control module 122 configured to move the test subject support 108 and thus the test subject 112 relative to the X-ray radiation source 104 and/or detector 110, and may also control motors in the gantry 102 or to position the X-ray illumination source 104 relative to the test subject 112 and/or the detector 110.

The controller 120 includes a detector controller 124 configured to control elements within the detector 110 and to facilitate data transfer therefrom. The controller 120 also includes a drive parameter controller 128 configured to control electrical drive parameters delivered to the X-ray radiation source 104. One or more computers 130 provide connections to the controller 120 via a bus 132 configured for receiving data descriptive of operating conditions and configurations and for supplying appropriate control signals, as will be described below in more detail with reference to Section II et seq. Buses 134 and 134' act to transfer data and control signals, for example with respect to a display-and-control module 135, via interconnections such as 134', such as to and/or from the computer 130.

The system 100 also includes a bus 136, a bus 138 and an operator console 140. The operator console 140 is coupled to the system 100 through the bus 134. The operator console 140 includes one or more displays 142 and a user input interface 144. The user input interface 144 may include a keyboard, a mouse or other tactile input device, capability for voice commands and/or other input devices. The one or more displays 142 provide video, symbolic and/or audio information relative to operation of system 100, user-selectable options and images descriptive of the test subject 112, and may include a graphical user interface for facilitating user selection among various modes of operation and other system settings.

The system 100 also includes memory devices 150, coupled via the bus 136 to the computer 130 through suitable interfaces. The memory devices 150 include mass data storage capabilities 154 and one or more removable data storage device ports 156. The one or more removable data storage device ports 156 are adapted to detachably couple to portable data memories 158, which may include optical, magnetic and/or semiconductor memories and may have read and/or write capabilities, and which may be volatile or non-volatile devices or may include a combination of the preceding capabilities.

The system 100 further includes a data acquisition and conditioning module 160 that has data inputs coupled to the detector 110 and that is coupled by the bus 138 to the one or more computers 130. The data acquisition and conditioning module 160 includes analog to digital conversion circuitry for capturing analog data from the detector 110 and then converting those data from the detector 110 into digital form, to be supplied to the one or more computers 130 for ultimate display via at least one of the displays 142 and for potential storage in the mass storage device 154 and/or data exchange with remote facilities (not shown in FIG. 1). The acquired image data may be conditioned in either the data acquisition and conditioning module 160 or the one or more computers 130 or both.

Development of portable digital x-ray radiation detectors, such as detector 110 and attendant digital signal/image processing chain 160 elements allows insertion of such into the context of existing analog X-Ray products, including mobile radiography systems, to alter the output signals/images from analog to digital formats. In doing so, a problem encountered is how to provide the actual interface between the existing analog x-ray radiation imaging product and the newly-introduced digital components. The data which must be transferred within the system include user selections (e.g., kVp, mA and mAs), data being displayed to the user without user input (e.g., battery level information or exposure indicator) or information normally hidden from the user (e.g., internal error messages or general input data). Thus, a programmable digital subsystem is needed that includes an advanced user interface within it to coordinate this via the display-and-control module 135 and/or the operator console 140 (e.g., touchscreen associated with display 142) and/or the computer 130, for controlling x-ray radiation technique selection and generator control in the modified analog imaging system 100.

Synchronous information transfer and modification of serial data between elements of the digital X-ray radiation image chain and within the existing mobile radiography system provides solutions to these problems by taking into account changing user and regulatory needs, and also facilitates system operation after replacement of one X-ray radiation detection system with a different X-ray radiation detection system having different signaling and other control and data protocols. The existing mobile radiography product 100 thus can become a mobile digital radiography (Mobile DR) product capable of being upgraded or modified.

In one embodiment, a field-programmable and reprogrammable interface module 137 may be inserted serially with the interconnection 134', at a juncture midstream in the useful service life of the system 100, possibly as one of several related modifications of the system 100, in order to modify functionality of the system 100 and the display-and-control module 135, and thus to accommodate enhanced capabilities of the system 100 realized through revised hardware or software modules that have been retrofitted or incorporated into the system 100. Addition of revised modules may present operational parameters, or operational parameter modifications, not comprehended by the original design goals for the system 100. Addition of the interface module 137, by facilitating modification of data exchanges appropriately, thus aids enhancement of system capabilities, without needlessly sacrificing ancillary components of the system 100.

The system 100 also includes a power supply 170, coupled via interconnections represented as a power supply bus 172, shown in dashed outline, to other system elements, and a power supply controller 174. In some embodiments, the system 100 is configured to be a mobile system equipped with a portable power supply 170, such as a battery. In other words, the system 100 may comprise a wheeled unit and may be electromotively powered in self-contained fashion, lending physical agility to the ensemble of attributes offered by the system 100.

In some settings, such as an emergency room, articulation of a mobility function may be limited to motion of a system 100 that is generally dedicated to application within that setting, suite or environment. In other settings, such mobility may include scheduled sequential visits to areas such as a cardiac unit, an ICU and other loci, where such imaging capability provides critical assistance, such as when the test subject 112 is not postured in a fashion consistent with movement of the test subject 112 and yet aperiodic variations in work load are not favorable to cost-effective deployment of a system 100 incapable of ready, self-propelled, operator-guided, "at need" physical translation of location. In one embodiment, electrically-powered motors coupled to a drive train effectuate operator-directed motion of the system 100.

Figure 2:
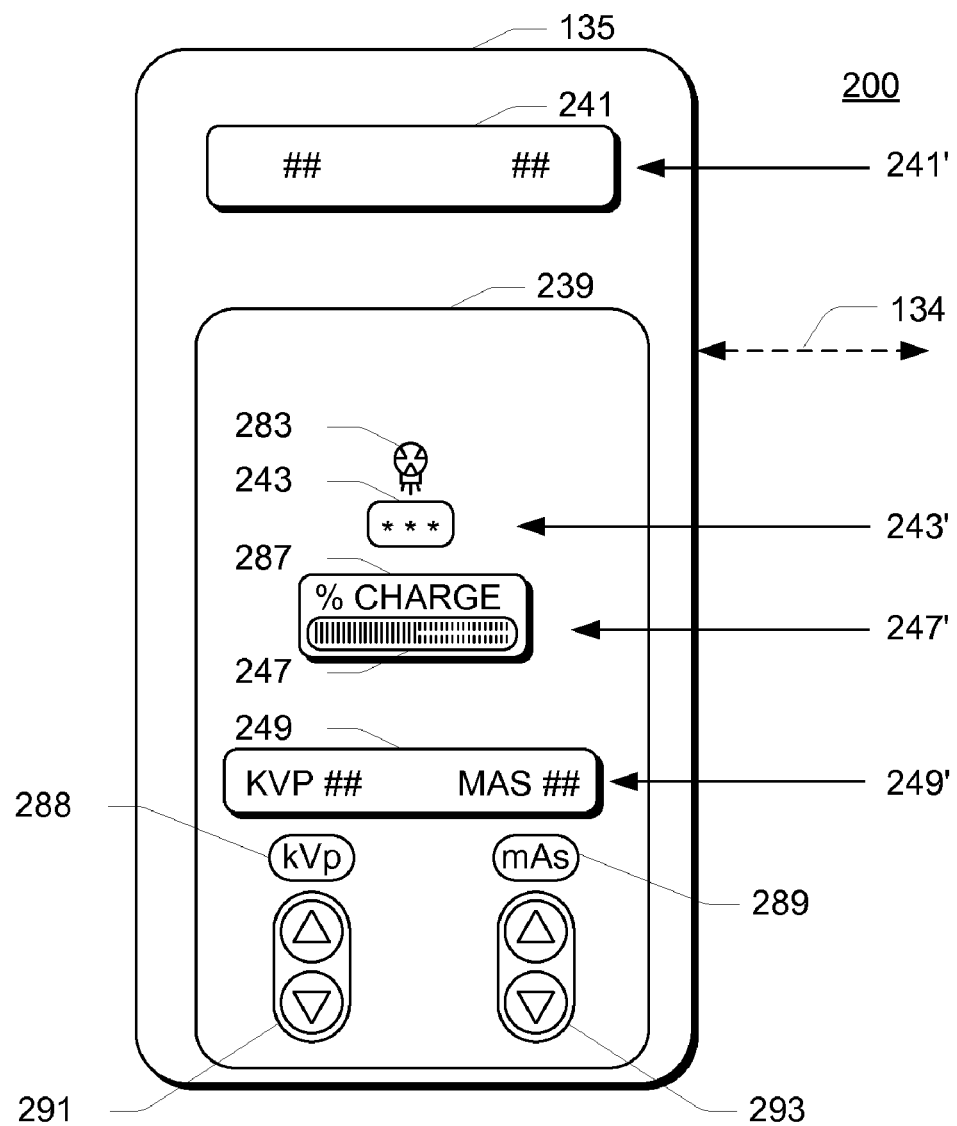
FIG. 2 is a simplified representation of a remote display and input/output element useful in the context of the system of FIG. 1.

FIG. 2 includes a simplified representation 200 of a bus 134 coupled to a remote display- and -control module 235 that is useful in the context of the system of FIG. 1. Bus 134 transfers data and control signals, for example with respect to the remote display-and-control module 235, through bus 134' as shown in FIG. 1, such as to and/or from the computer 130. The remote display-and-control module 235 includes a control/display panel 241 and may include more than one hand-portable unit. For example, in the context of an X-ray radiation imaging system 100, a physically separate hand-holdable switch (not explicitly shown in FIG. 1 or 2) may be usefully employed for triggering energization of the X-ray radiation source 104 via operator control.

The remote display-and-control module 235 includes optical displays 241, 243, 247 and 249 configured to display indicia 241', 243', 247' and 249', respectively, indicative of status of various elements of the system 100. The remote display-and-control module 235 includes indicia 283, 287, 288 and 289 as well as tactile input elements 291 and 293.

The optical display 241 provides indicia 241' descriptive of system drive settings relative to the X-ray radiation source 104, which settings are adjustable via the tactile input elements 291/293 in cooperation with the selected settings as displayed on optical display 249, but which may alternatively be determined by other system elements, subject to operator confirmation via user review, in conformance with particularized imaging tasks, empirical data from prior measurements or images and the like. The optical display 249 provides indicia 249' of user-selected settings as such settings are modified or set by a system operator.

The optical display 247 provides indicia 247' of consumable or renewable system resources, such as remaining useful battery capacity, in the example of FIG. 2 and as denoted by markings 287. In one embodiment, the optical display 247 comprises a bar-graph display (in conformance with the example of FIG. 2) such as a multiple-segment bar-graph display element, shown at approximately fifty percent in this example, as denoted by the display elements in full line form at the left half of the display 247 and the display elements in dashed line form at the right half of the display 247.

The marking 283 indicates in language-independent form that the optical display 243 corresponds to activation of system elements that require appropriate caution in operation, such as the X-ray radiation source 104 of FIG. 1. Auditory signals often also are contemporaneously employed to affirmatively denote activation of such sources, due to harmful cumulative effects that may preferentially offer danger to operators of such systems.

In usage, desired settings selected via the remote display-and-control module 235 as shown in the display 249, or selected via the operator console 140, and then are communicated to the system 100 via signals, and system system-selected settings are received by the remote display-and-control module 235 as noted on the display 241. These settings are reviewed, and values corresponding to the selected settings are stored along with data/images from operation of the system 100. The stored data, system settings, information denoted by indicia 241' and 249', and information shown by the operator console 140, should all agree, for effective system operation. In turn, data associated with these aspects are synchronized via adaptive system elements, such as are described below in Section II.

II. Adaptive System Elements

In this section, adaptive and programmable aspects applicable to the system of FIGS. 1 and/or 2 of Section I, supra, are described. It will be appreciated that, while these concepts as disclosed and enabled below are phrased in terms of conventions such as particularized embodiments, other forms of description and other applications are applicable and may be employed, without significantly altering the teachings of the present disclosure.

Figure 3:
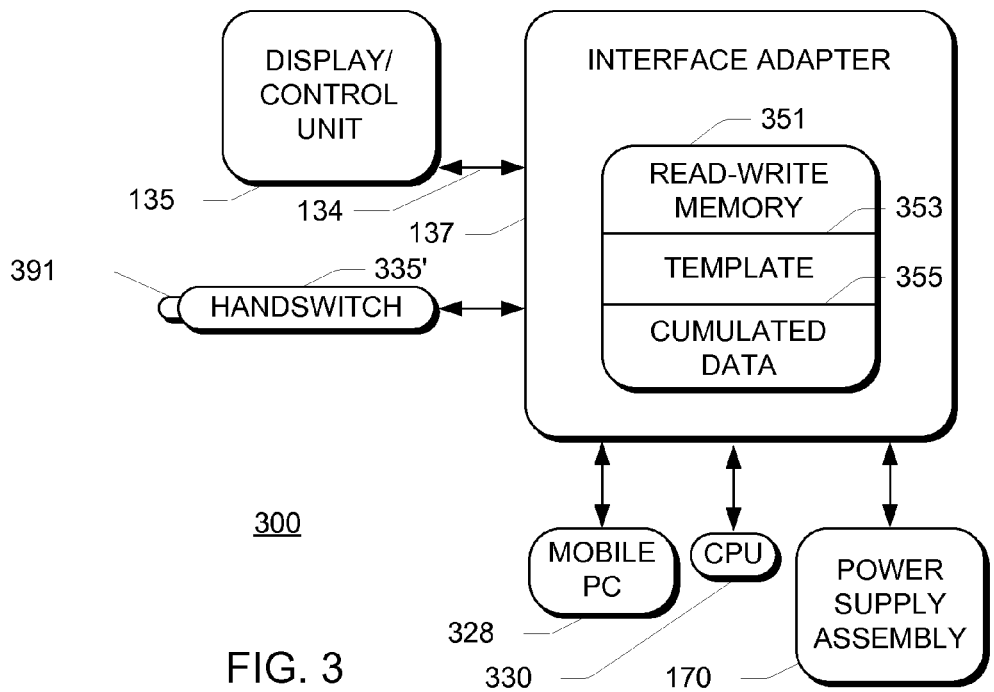
FIG. 3 is a simplified block diagram illustrating an interface adapter element and relationships to other system components that is useful in the context of the system of FIG. 1.

FIG. 3 is a simplified block diagram illustrating interface adapter elements 300 and relationships to other system components, useful in the context of the system 100 of FIG. 1. The interface adapter elements 300 provides an information and signal expansion mechanism, as is explained below. In FIG. 3, a mobile personal computer 328 and a central processing unit 330, similar in functional aspects to the computer 130 of FIG. 1, are depicted, coupled via a bus 134, to a remote display, control and input/output element 135 and/or a remote handswitch 335' through an interfacing module 137 containing a programmable memory 351 including a template portion 353 and a cumulative data portion 355.

The template portion 353 includes information descriptive of a current system configuration, as well as computer-readable instructions relevant to operating characteristics and commands associated with elements comprising the system 100, and may be provided with additional information by qualified personnel at such time as the system 100 is reconfigured. The cumulated data portion 355 maintains current information relative to operation of the system 100, as well as a running historical record relevant to subsystem components within the system 100.

A power supply assembly 170 provides status signals via the interfacing module 137. The pushbutton 391 coupled to the handswitch 335' provides operator control as a fail-safe act for triggering X-ray radiation generation for imaging, in conformance with operator inspection of various displays, such as those described with reference to FIG. 2 and/or monitor/display 142 of FIG. 1.

The interface adapter elements 300 may, for example, modify signaling and other functional aspects of cooperation between elements of the system 100 in conformance with added or replaced elements. For example, when an analog detection system originally supplied as a portion of the system 100 is replaced with a digital detection system, such as the detector 110 of FIG. 1, the control signals, system commands and status signaling, system power consumption variables and system capabilities may be modified in ways that could not have been envisioned at the initial stage of system design and thus could not be comprehended in the sensors and other operative elements when the system 100 was initially constructed.

Thus, field-programmable interface elements, such as the interface adapter/module 137 of FIG. 3 and FIG. 1 may be employed in order to accommodate these revised system capabilities and to promote harmonious co-integration of the added modules within the existing infrastructure. These revisions may be accomplished even when the added system elements derive from independent manufacturers and do not include detailed co-integration data at all system levels associated with robust system functionality on multiple levels. In other words, the interface adapter/module 137 provides for expansion of capabilities that the system 100 was originally capable of, and for updating of signaling and displays in conformance with the expanded or modified system attributes.

As a result, the original purchaser or current owner of such a system 100 is able to leverage successful prior product deployment and investment to achieve increased functionality in conformance with subsequent decisions by that purchaser. Further, such capabilities are achieved without incurring undue penalty that might otherwise accrue as a result of varying manufacturing standards, compatibility factors and protocols. In turn, such can provide particularly beneficial applications to which X-ray radiation imaging and other medical diagnostic systems are generally directed.

The interface adapter elements 300 include capability for coupling signals and data between infrastructural elements such as the mobile computer or PC 328 and/or the central processing unit 330 and control elements such as the display/control unit 135 and handswitch 335', and for expansion of input/output capabilities. Typically, interconnections to elements such as mobile computer 328, central processing unit 330, display/control unit 135 and handswitch 335' represent infrastructural elements associated with prior system embodiments of the system 100.

The interconnections may support serial signal exchange protocols, which may be synchronous or asynchronous serial data protocols, and may include parallel signaling capacities. The interface adapter 137 includes, among other things, information contained within the read/write memory 351, providing signal/data translational capabilities between system elements, including those comprising the system 100 prior to system modification, in view of considerations provoked as a result of system modification via hardware and/or software changes.

The read/write memory 351 may comprise a conventional field-programmable gate array, for example, that is updatable via data supplied by field service technical experts. Field-programmable gate arrays are known in the art and are commercially available from, for example, Xilinx, having headquarters at 2100 Logic Drive, San Jose, Calif. 95124-3400; Opera of Oslo, Norway; Altera, headquartered at 101 Innovation Drive, San Jose, Calif. 95134; and other manufacturers and vendors.

Such data may be introduced as modulation on a carrier wave embodying various types of computer or machine interpretable instructions. A removable data storage device 158 or detachable computer readable medium, such as an optical disc (CD or DVD) or other data source, may be coupled to the system 100 via a removable storage port 156, for example, or such instructions may be supplied via other, authorized, mechanisms, such as through a remote data source or a remote computer (discussed below with respect to FIG. 9), the Internet or other appropriate and approved sources, and may be applied directly to the interface adapter 137.

The read/write memory 351 may also include non-volatile memory elements, such as FLASH memory, capable of storing data representative of current status of one or more system elements. Examples of such data may include a number of times that the system 100 has been activated, for example, after one or more power supply elements 170 have been replaced, or data indicative of depth of discharge of such power supply elements 170 relative to a most-recent recharge cycle and/or other related data, data specifically descriptive of present system configuration (type of detector, for example, and associated power requirements and/or typical operating parameters, date of installment or service/update of various system components) and may also optionally include data descriptive of ambient operating system conditions (temperature, achieved power supply voltage level, measured current draw from the power supply etc.).

Process embodiments operative with the system 100, remote module 135 and the interfacing adapter elements 300, together with benefits associated with their cooperative engagement, are described below in more detail in Section III, with reference to FIGS. 4 and 5.

III. Process Embodiments

In the previous section, modules capable of intercalation between elements of previously-existing systems in furtherance of functionality with respect to system modifications were described. In this section, the developments and adaptations of that section are further employed as vehicles for describing the operation of a series of embodiments, with the particular processes of such embodiments being described by reference to relevant flowcharts. Describing the processes by reference to one or more flowcharts enables one skilled in the art to develop programs, firmware, or hardware, including such instructions configured to effectuate the processes, as well as subsequent revisions, through one or more processors responsive to computer-readable instructions embodied on computer-readable media.

These capacities are often accomplished using suitable computers, including one or more processors, by executing the instructions embodied in articles of manufacture such as computer-readable media. As a result, the computer-readable instructions may include capacity for accepting revised computer-readable information descriptive of revised capabilities, which may relate to revisions of aspects of the system 100 via substitution of components, revisions of data-processing structures and the like. Similarly, processes performed by server computer programs, firmware, or hardware also are represented by computer-executable instructions. The processes of the present disclosure are performed by one or more program modules executing on, or performed by, firmware or hardware that is a part of a computer (e.g., computer 130, FIG. 1), and/or interface adaptive elements 300.

In some embodiments, processes disclosed herein are implemented as embodied in a device that represents a sequence of instructions which, when executed by one or more processors, such as a processor contained in or associated with the computer 130 in FIG. 1, causes the respective process to occur. In other embodiments, the processes disclosed herein are implemented as a computer-accessible medium having executable instructions capable of directing a processor, such as one or more processors contained in or associated with the computer 130 in FIG. 1, to perform the respective process. In varying embodiments, the medium is a magnetic medium, an electronic medium, or an electromagnetic/optical medium.

More specifically, in a computer-readable program embodiment, programs can be structured in an object-orientation using an object-oriented language such as Java, Smalltalk or C++, and the programs can be structured in a procedural-orientation using a procedural language such as COBOL or C. Software components may communicate in any of a number of ways that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 130 in FIG. 1, or on multiple computers.

Figure 4:
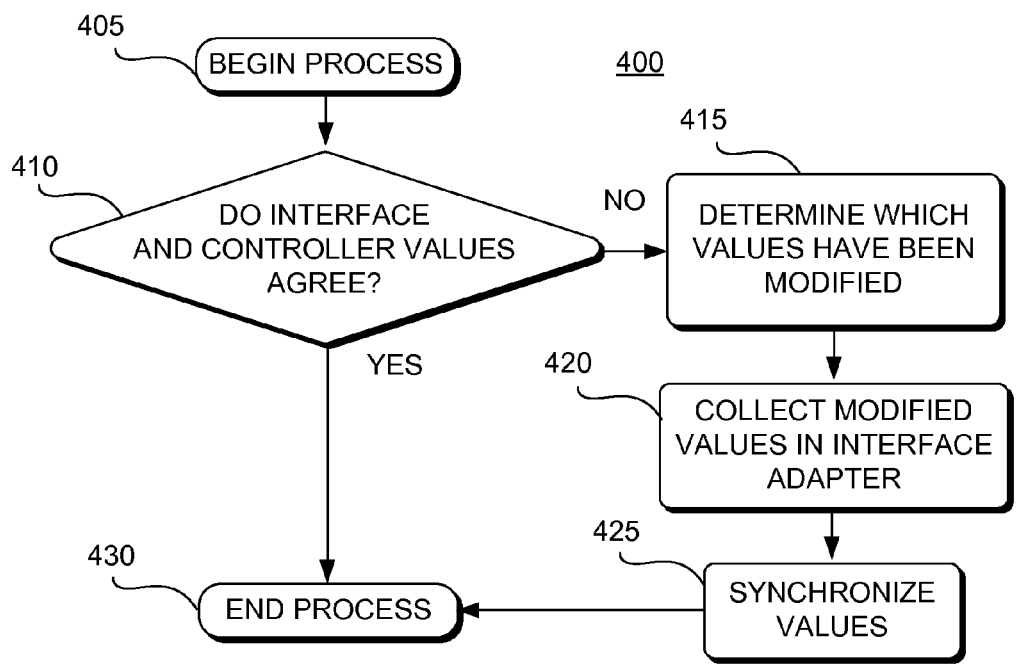
FIGS. 4 and 5 are flowcharts describing processes capable of utility in the system of FIG. 1.
Figure 5:
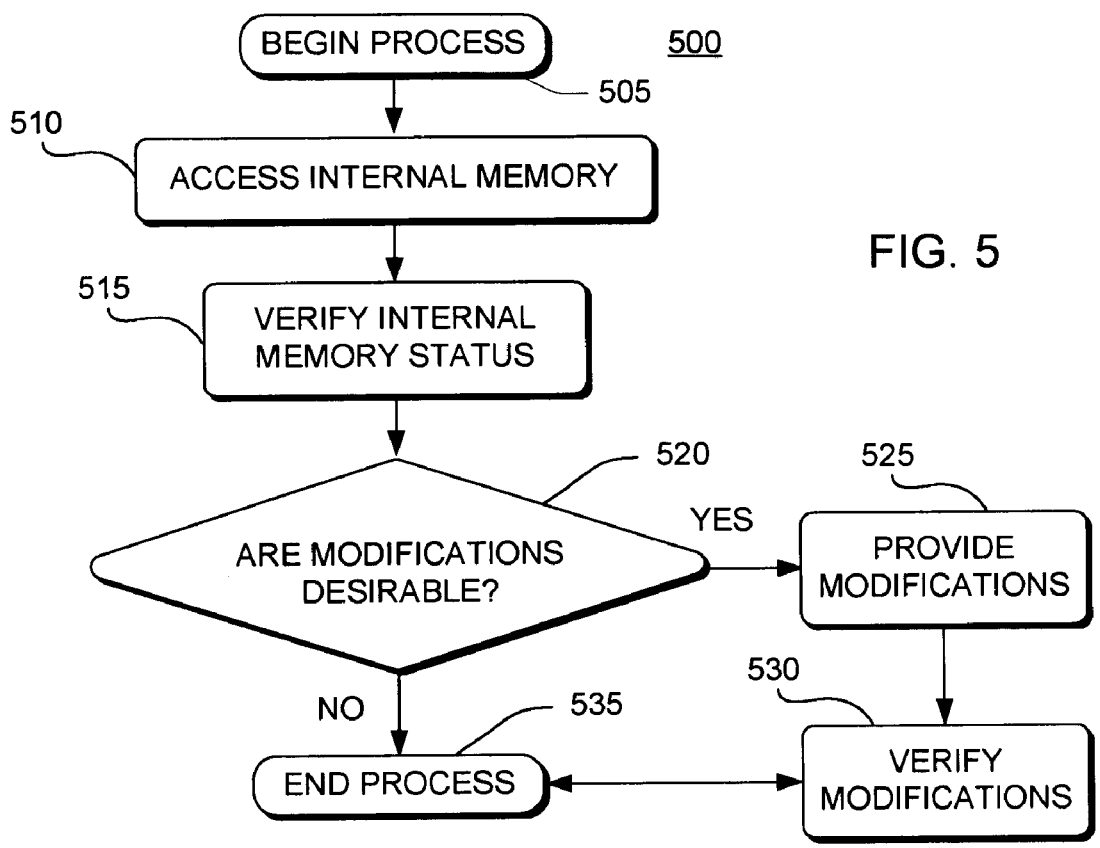

FIGS. 4 and 5 are flowcharts describing processes 400 and 500, respectively, capable of utility in the system 100 of FIG. 1. The processes 400 and 500 described above may be implemented as hardware or software or a combination thereof. The processes 400 and 500 may be updated via addition or substitution of machine-readable and executable instructions in computer-based controllers, as is described below in more detail in Section VI, with reference to FIG. 9.

FIG. 4 shows a flowchart of a process 400 configured for coordination of values associated with the display/interface 142 of FIG. 1, the remote display and input/output element 135 of FIG. 2 and values represented in the computer 130 of FIG. 1, for example. The process 400 begins in a block 405.

In a query task 410, the process 400 determines when one or more values associated with the computer 130, the operator console 140 and/or the input/output element 135 do not agree or have been modified. These values may be system-suggested or default field values (e.g., derived via the computer 130), or values entered by an operator via either the remote display and input/output element 135, a touchscreen or other I/O device associated with the display 142, for example. Those values selected may be outside of a range of values consistent with those associated with the system 100 at initial deployment, but within an expanded range of values made available via additions or modifications to the system 100, for example, as reflected in data entered into the read/write memory 351 of the interface adapter 137 and thus within a range of present system 100 capabilities. The values may be kVp values, mA values or other values pertinent to a measurement being undertaken.

When the query task 410 determines that disagreement between these values exists, control passes to a block 415. In the block 415, the process 400 determines which of the values has been modified. For example, a peak voltage modification or a current modification or other drive parameter modification for the illumination source 104 of FIG. 1 may be appropriate in view of modifications to the system 100 and may have been altered on one or more of the operator console 140, the display and I/O element 135 or by the computer 130. Control then passes to a block 420.

In the block 420, the modified values are collected in the interface adapter 137 of FIG. 3. These values are compared to stored values and system commands, which stored data may be alterable via the process 500 of FIG. 5, described below. Control then passes to a block 425.

In the block 425, the interface adapter 137 coordinates parameter values between the various system components. As a result, parameter values that are sent to, and thus displayed on, the operator console 140 and/or the input/output element 135, agree, and also agree with data associated with any diagnostic images formed and then processed via the computer 130, for example. Additionally, the interface adapter 137 may be programmed to suppress some forms of system data, which are relayed to other portions of the system 100 as appropriate.

The process 400 then terminates in a block 430. Also, when the query task 410 determines that the values do agree, the process 400 terminates in the block 430.

FIG. 5 shows a flowchart of a process 500 configured for updating variables relative to operation of the system 100, responsive to modifications of hardware, either to actualize desired system capabilities or that are consistent with replacement of consumable elements within the system 100, which replacements may be "like-kind" or which may represent distinction in terms of one or more operational parameters relevant to operation and/or maintenance of the system 100. The process 500 begins in a block 505. Initiation of the process 500 may result from a stand-alone software or instruction set modification or may be reflective of system modification, either including elements not previously incorporated within the system 100 or as an aspect of routine replacement of consumable items, such as batteries 170 that have provided the appropriate reliable useful service life consistent with appropriately robust operation of the system 100.

In blocks 510 and 515, an internal non-volatile memory is accessed and verified. For example, such may be a memory internal to the system 100 and/or may include a field-programmable gate array comprising a portion of the read-write memory 351 of FIG. 3, and may include redundant but separate non-volatile memory elements, such as the memory system 150 of FIG. 1. Control then passes to a query task 520.

In the query task 520, a determination is made with respect to desirability of modification of one or more stored data elements (such as identities and operational data specific to system components which may be replaced or upgraded as a portion of field service). Such evaluation is generally effectuated in conformance with contemporaneous review via qualified service personnel, and may range from quotidian maintenance elements (replacement of batteries with similar or different battery types) to more complex system modifications (replacement of a processor, or even an entire image detection and processing ensemble, such as providing a digital detector array and concomitant signal processing apparatus in lieu of originally-supplied, then state-of-the-art, analog detector assemblies and signal processors).

When the query task 520 determines that modification is desirable and are approved, control passes to a block 525. In the block 525, modified data and/or instruction sets are made available to the system 100 and/or the read-write memory 351 and are included within the system 100. Control then passes to a block 530.

In the block 530, the modification is verified. As such, modification of system data typically includes: (i) determination of operational status of the memory system to ensure reliability; (ii) review of version and configuration of system descriptors stored in that memory; (iii) comparison of those descriptors to other information, including revised or revisable system parameters; (iv) provision of or revision of revised data, instruction sets and/or calibration data relevant to current system configuration; and (v) verification of receipt of revised information.

When the query task 520 does not determine that modification is desirable, or when the acts associated with the blocks 525 and 530 have been executed and verified, control passes to a block 535. The process 500 then is concluded, and other system functions continue or are initiated.

Advantages realized by the disclosed processes, concepts and subsystems including at least the following seven benefits:

1. Changes made on either user interface, i.e., on the I/O unit 135 or the operator console 140, are contemporaneously coordinated throughout the system 100. Similarly, all technique displays, such as 241/243/247/249 and the monitor 140, always display coordinated data or the same information.

2. The interfacing module 137 verifies coordination of the kVp and mA selections between the I/O unit 135 and the computer 130. The computer 130 then utilizes the techniques for the image processing and updates the monitor display 142.

3. The interfacing module 137 sends the kVp and mA selections to the I/O unit 135 from the computer 130. The interfacing module 137 then transmits the selected techniques to the system controller/computer 130, as though the user has selected the techniques on the I/O unit 135.

4. The interfacing module 137 intercepts all control and data signals exchanged between the computer 130 and the I/O unit 135, and thus can then relay other system messages (typically displayed on the I/O unit 135) to the computer 130 for the digital system usage. These messages would be for the user concerning shutdown status, error messages, battery warnings, exposure message, etc.

5. Since the interfacing module 137 can write messages to the I/O unit 135, it can add new message pertaining to the Digital Image Chain which did not previously exist on the system 100. These messages would be for the user concerning digital system faults, user requested shutdown from the operator console 140, digital image error messages, etc.

6. The interfacing module 137 sends the kVp and mAs selections from the I/O unit 135 to the computer 130. The computer 130 then utilizes the techniques for the image processing and updates the monitor display 142.

7. The interfacing module 137 can transmit any general system I/O information present as discrete parallel I/O or data on the serial interface to the computer 130.

In particular, issues involving system modifications via inclusion of modules from vendors and manufacturers other than that which initially produced the system 100 are accommodated and may be seamlessly integrated and comprehended via suitable software modifications. However, besides the technique data, all the general purpose I/O signals used to transmit status for system elements including collimator, hand-switch 335', interlocks, drive handle, and other useful components can also be supplied to the computer 130 using the processes and apparatus disclosed herein. Such integration provides increased functionality and programmability for the modified system 100.

IV. Graphical User Interfaces (GUIs)

Figure 6:
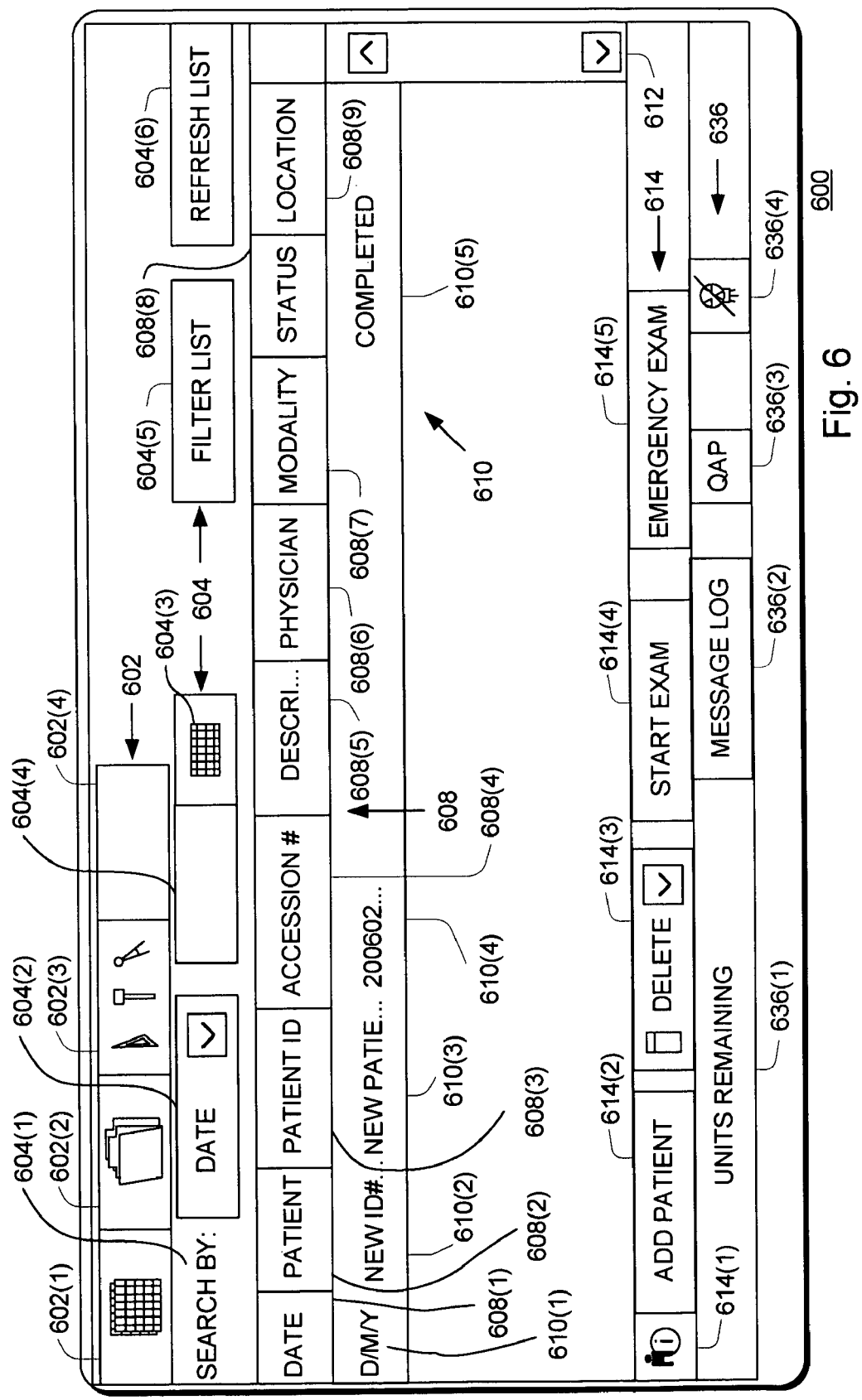
FIGS. 6, 7 and 8 depict graphical user interfaces capable of utility in the system of FIG. 1.
Figure 7:
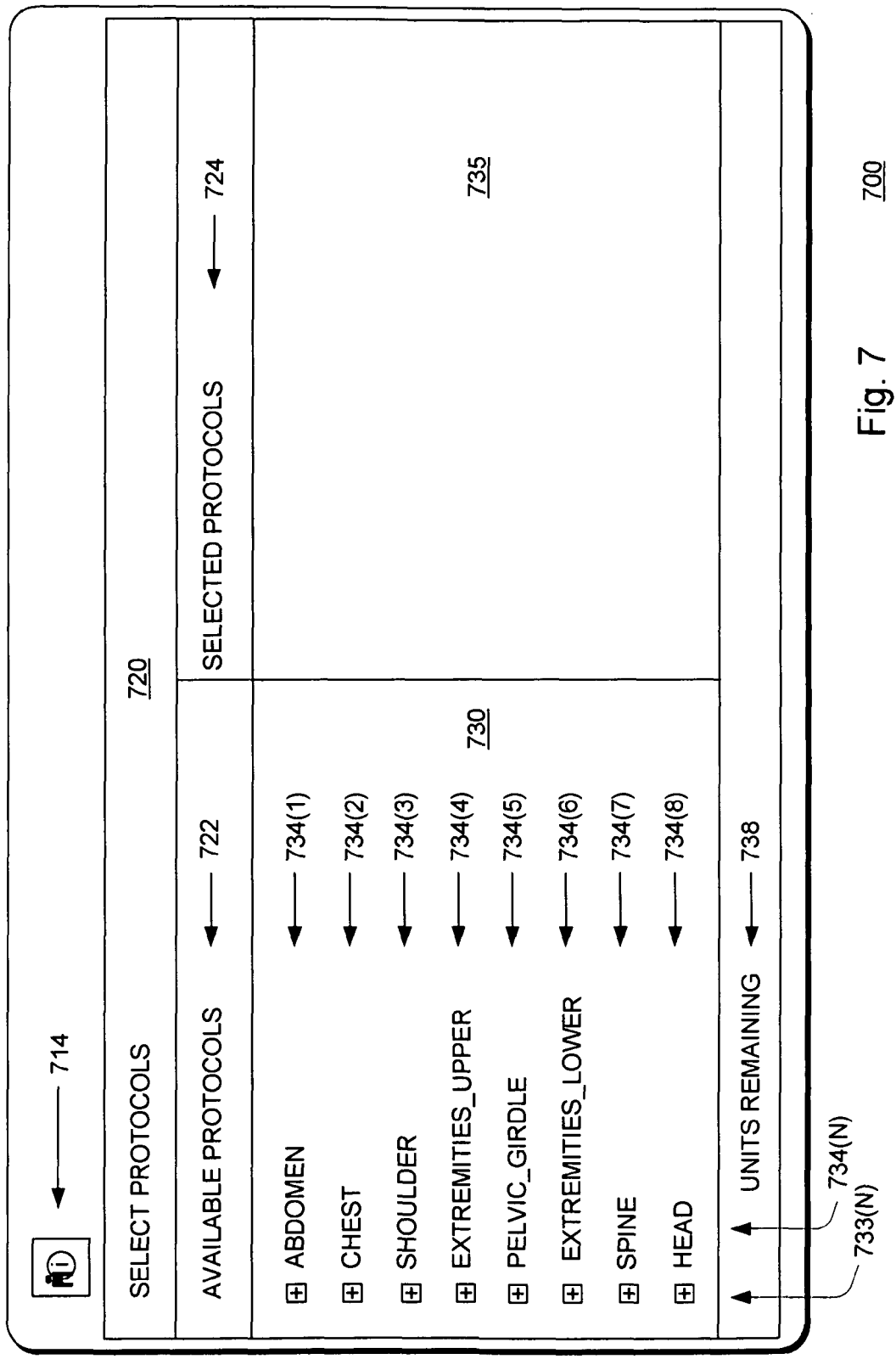
Figure 8:
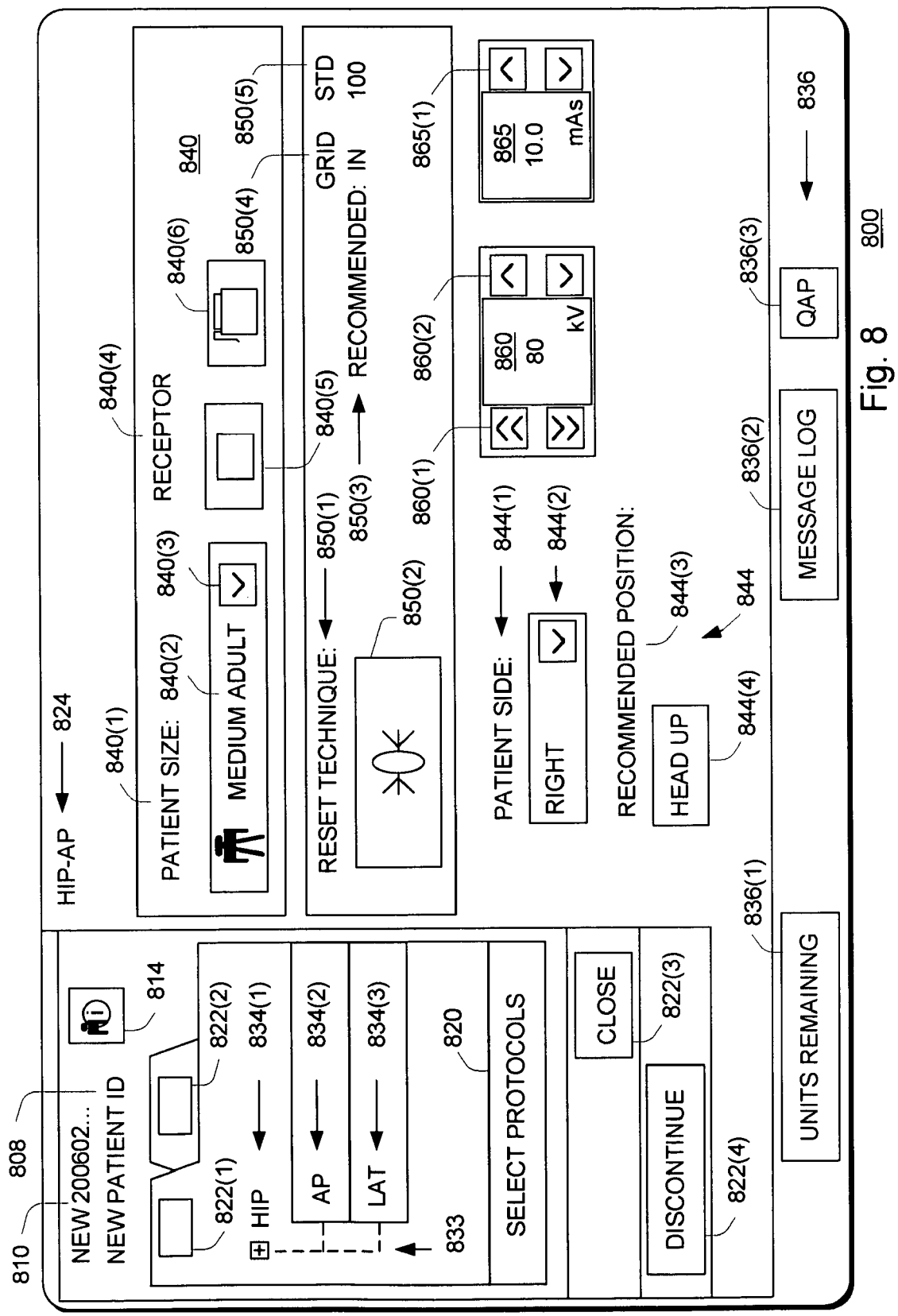

FIGS. 6, 7 and 8 depict GUIs 600, 700 and 800, respectively, that are capable of utility in the system of FIG. 1. The exemplary GUI 600 of FIG. 6 allows patient data to be selected or entered, facilitates record searching and provides other functionality, which functions and capabilities may be modified via the process 500 of FIG. 5, for example, to reflect modifications to the system 100 and to maintain data coordination as between, for example: (i) the I/O module 135 (FIG. 1)/remote display and input/output element 135 (FIG. 2); (ii) the display 142 in the operator console 140 (FIG. 1); and (iii) records stored in memory 150 (FIG. 1) and/or transmitted to remote locations for purposes of collaboration or other reasons, in order to promote mutual conformance and to ensure that each accurately reflects parameters descriptive of the measurement.

The GUI 600 usefully includes general-purpose tools 602, which may include a calendar icon 602(1), a folder icon 602(2), a tool icon 602(3) and/or other system function icon areas 604(4). The GUI 600 also may include organizational tools 604, such as a search menu 604(1), a search by date pull-down menu 604(2), a virtual keyboard icon 604(3) and/or a text entry window 604(4). In one embodiment, the virtual keyboard icon 604(3), when touch-activated, enables text entries which are presence/absence inferable via the text window 604(4), and which may include or affect a filter list function 604(5) and/or refresh list function 604(6).

A record information bar 608 may be included, as shown in the example of FIG. 6, below the organizational tools area 604. The record information bar 608 may include descriptive fields such as a date field label 608(1), a patient name field label 608(2), a patient identification field label 608(3), an accession number field label 608(4), a description field label 608(5), a physician name field label 608(6), a modality description field label 608(7), a status field label 608(8) and/or a location field label 608(9), for example.

A data display bar 610 is illustrated as being below the record information bar 608 in FIG. 6. The data display bar 610 may include data entries corresponding to selected associated ones of data record fields 610, such as a date field D/M/Y 610(1), a patient identification field NEW ID# . . . 610(2), a patient name field NEW PATIE . . . 610(3), an accession number field 200602 . . . 610(4) and/or a status field 610(5), stating "COMPLETED" in this example.

The information associated with the information bar 608/ data display bar 610 may be modified by qualified technicians when the system 100 is modified, in association with periodic maintenance, or in association with aperiodic system capabilities modifications, for example as described above with reference to the process 500 of FIG. 5, and the synchronization capacities of the interface adapter 137 of FIG. 3 may also be contemporaneously augmented via software modification. Alternatively, such coordinated software modifications may be effectuated via one or more remote computers, such as an embedded web server or other controller, as is described below in more detail in Section V with reference to FIG. 9.

In one embodiment, the filter list function, such as may be referenced via the icon 604(5), facilitates searching using a selected one or ones of the descriptive fields 608(N). For example, records may be searched and then displayed in conformance with organization by physician name, facilitating extremely rapid access to stored information in a manner consistent with a user-specified set of search criteria.

The GUI 600 also may include a conventional scroll bar 612 that facilitates modification of displayed elements within a particular GUI 600 in conformance with selections provided via conventional tactile/sensory input modalities, such as a keyboard functions, a touch screen, mouse or voice commands, among others. A series of system command icons 614 may be provided and may usefully include, for example, a patient information icon 614(1), an "add patient" functionality access point 614(2), a delete functionality access point 614(3), a start exam functionality access point 614(4) and/or an emergency exam functionality access point 614(5).

In one embodiment, the patient information icon 614(1) may be touch-screen activatable and/or accessible via other tactile input device, voice-activated activation mechanism etc. In one embodiment, activation of the patient information icon 614(1) may provide access to general patient information.

The GUI 600 may also include a status and system-level indicia display 636, which may provide indication of units remaining 636(1), a message log area 636(2), a QAP area 636(3) and an "exposure inhibit" indicator 636(4) showing when an X-ray radiation source 104 cannot presently be energized, for example.

The "exposure inhibit" indicator 636(4) employs an IEC symbol for showing when an X-ray radiation source such as the X-ray illumination source 104 of FIG. 1 cannot be energized by the system 100, i.e., is "locked out" by protocol for any of a variety of safety reasons, or is inconsistent with the physical status of the system 100 or is incompatible with a stage in the procedural scenario. In the example of FIG. 6, it is inappropriate to energize the X-ray radiation source 104 while the GUI 600 is being displayed, because conditions precedent to energization have not been met at this juncture. With respect to the graphical user interface 800 of FIG. 8, infra, however, display of an "exposure inhibit" indicator such as 636(4) is an indication that an operator should touch the indicator location on the screen in order to review a display of those conditions that render result in the system 100 precluding such energization. Following data entry/verification via the GUI 600, a GUI 700, such as the example illustrated in FIG. 7, is shown to the user.

The GUI 700 of FIG. 7 shows a digital image exam screen adapted to facilitate protocols appropriate for selection of anatomy examination relevant to the presenting patient, as identified via data entries using the GUI 600 of FIG. 6, for example. The GUI 700 includes a patient information icon 714 like the patient information icon 614(1) of FIG. 6, a modality indication field 720 displaying "SELECT PROTOCOLS" in the example of FIG. 7, an available protocols header 722, and a selected protocols header 724.

The GUI 700 also may include a protocol field 730, including selection buttons 733 and indicators 734 for selecting among examples of protocols such as ABDOMEN 734(1), CHEST 734(2), SHOULDER 734(3), EXTREMITIES_UPPER 734(4), PELVIC_GIRDLE 734(5), EXTREMITIES_LOWER 734(6), SPINE 734(7) and HEAD 734(8). It will be appreciated that this listing of protocols is exemplary, and that more or fewer protocols may also be included within a menu of protocols accessible, for example, via the modality indication field 720 and/or the protocol field 730. It will also be appreciated that the protocols available may be modified via the process 500 of FIG. 5, for example, in conformance with modifications of the system 100 or the software employed in analysis of images from the system 100, and suitable programming of the interfacing module 137 of FIG. 3, for example. As a result, the interfacing module 137 is able to support modified system functionality and to promote mutual conformance between the data shown via the I/O module 135 and that associated with the operator console 140 display 142 (FIG. 1), data stored in the data storage module 150, the remote display and input/output element 135 (FIG. 2) and/or the display/control unit 135 of FIG. 3.

Data corresponding to a selected protocol may be displayed in a data field 736, for example, to provide indication as to data that may be stored along with images associated with the patient and other information described above with reference to FIG. 6 and one or more protocols as described with reference to the GUI 700. The GUI 600 may also include a status and system-level indicia display 738, such as UNITS REMAINING in this example. Following data entry/verification via the GUI 700, a GUI 800, illustrated in FIG. 8, is shown to the user.

The GUI 800 of FIG. 8 shows a digital image exam screen adapted to facilitate protocols appropriate for selecting exposure parameters, such as kVp, mAs, protocols, and the like, for the system 100 of FIG. 1. The GUI 800 includes a NEW PATIENT ID label 808, an NEW PATIENT ID field 810 displaying "NEW 200602 . . . " in this example, a patient information icon 814 is like the patient information icon 614(1) of FIG. 6, a SELECT PROTOCOL label 820 that is accessed via command labels or folder tabs, such as folder tabs 822(1) and 822(2), and which is deaccessed via button CLOSE 822(3) or button DISCONTINUE 822(4). A label 824 displays a selected one of the protocols. Selecting the folder tab 822(1) allows access to a menu of protocols, via buttons such as button 833, for example, HIP 834(1), anterior/posterior "AP" 834(2), lateral LAT 834(3) etc.

System control functions are displayed in a display bar 836, including UNITS REMAINING 836(1), MESSAGE LOG 836(2) and QAP 836(3). A control panel 840 includes selection areas and labels, such as the label "PATIENT SIZE:" 840(1), a label showing a selected size, labeled "MEDIUM ADULT" 840(2) and a scroll bar 840(3), a label "RECEPTOR" 840(4), and icons/selection buttons corresponding to a film cassette 840(5), or a digital detector, such as a floating receptor 840(6), corresponding to a selected type of receptor. An information display area 844 provides information relative to the type of exam being performed, in this example as shown by the label "PATIENT SIDE" 844(1), the information "RIGHT" and an associated scroll bar 844(2), a label "RECOMMENDED POSITION" 844(3) and a display "HEAD UP" 844(4).

The GUI 800 also includes a display area 850, showing a label "RESET TECHNIQUE" 850(1) identifying a button 850(2) (which resets the system to default values when selected), a label "RECOMMENDED" 850(3), showing a GRID parameter 850(4) ("IN" in this case), and STD ("100" in this case). A control/display area 860 relative to kVp (and showing "80" in this example) includes scroll bars 860(1) and 860(2), and another control display area 865 relative to milliAmpere-seconds (and showing "10.0" in this example) includes scroll bars 865(1) and 865(2). The GUIs 600, 700 and 800 thus provide user-selectable data and control entry functions in a logical sequence for providing/accessing patient information and data and values pertinent to an exam to be performed, and these functions are reprogrammable in conformance with modifications to the system 100 as described above.

System functionality and operation thus may be effectuated via the GUI sequence 600, 700, 800, for example via a touchscreen, and selections so determined may be synchronized between all elements of the system 100 via the interfacing module 137. System capabilities may be expanded via programming of suitable instructions and data, for example as described with reference to the process 500 of FIG. 5, in memories such as the memory 351 of FIG. 3 and/or 150 of FIG. 1. Additionally, a gamut of aspects accessed via or represented by the GUIs 600, 700, 800 may be altered or expanded via such programming.

As a result, the system 100 is provided with revised data and instructions. Continuity of capabilities of the system 100 are augmented, and performance, as well as longevity of the system 100, are promoted. As an example, a technical effect promoted by such can include capability of transmission, via digital technologies, of radiographic images having improved diagnostic value for immediate contemplation and evaluation by experts during triage, or even during transportation of a victim of an accident from the situs of the disaster to suitable medical facilities—such as during the "golden moments" immediately following determination of injury that are extremely vital to increasing patient survival, as well as recovery trajectory. These features and advantages can represent significant improvements in system performance, from a capabilities perspective as well as reliability considerations. Such enhancements, in terms of machine-controlled performance in tandem with operator review and approval, may be achieved via the elements described above with reference to FIGS. 1 through 8, as well as in conjunction and cooperation with an operating environment such as that which is described below in Section V with reference to FIG. 9.

V. Hardware and Operating Environment

Figure 9:
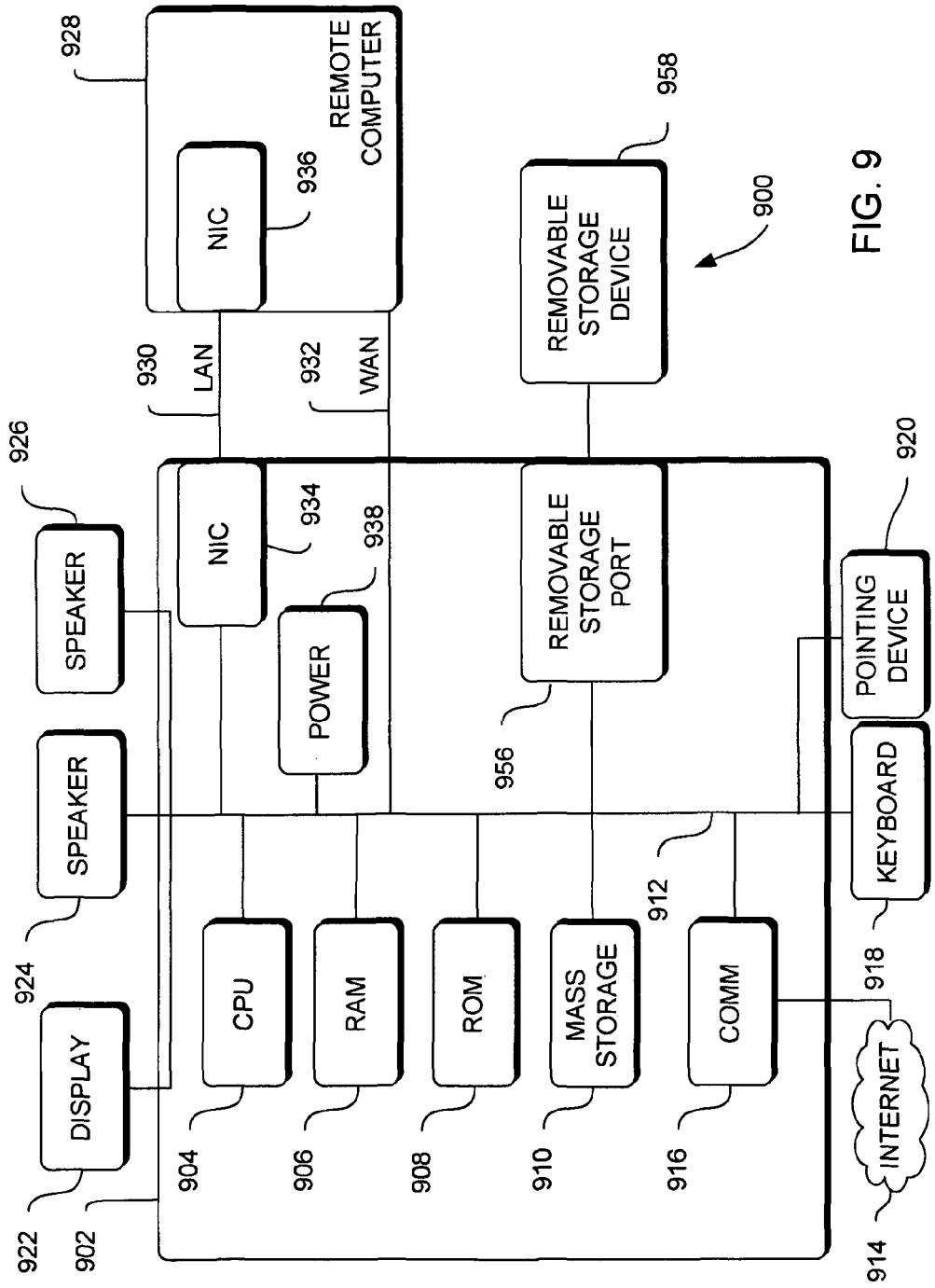
FIG. 9 is a block diagram of a hardware and operating environment in which different embodiments can be practiced.

FIG. 9 is a block diagram of a hardware and operating environment 900, including one or more computers 902, in which different embodiments can be practiced. The description of FIG. 9 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

The computer 902 includes one or more processors 904, commercially available from Intel, Santa Clara Calif.; Motorola, Schaumburg Ill.; Cyrix, now associated with National Semiconductor of Santa Clara Calif.; and others. The computer 902 also includes random-access memory (RAM) 906, read-only memory (ROM) 908, and one or more mass storage devices 910, and a system bus 912, that operatively couples various system components to the processing unit 904 and/or to each other and/or external apparatus. The memories 906 and 908, and the mass storage devices 910, are types of computer-accessible media. Mass storage devices 910 are more specifically types of nonvolatile computer-accessible media and can include one or more hard disk drives, floppy disk drives, optical disk drives, and tape cartridge drives. The processor 904 executes computer programs stored on these various computer-accessible media.

The computer 902 can be communicatively connected to the Internet 914 via a communication device 916. Internet 914 connectivity is well known within the art. In one embodiment, a communication device 916 is a modem that responds to communication drivers to connect to the Internet via what is known in the art as a "dial-up connection." In another embodiment, the communication device 916 includes an Ethernet® or similar hardware network card connected to a local-area network (LAN) that itself is connected to the Internet 914 via what is known in the art as a "direct connection" (e.g., T1 line, etc.).

A user enters commands and information into the computer 902 through input devices such as a keyboard 918 or a pointing device 920. The keyboard 918 permits entry of textual information into computer 902, as known within the art, and embodiments are not limited to any particular type of keyboard 918. The pointing device 920 permits the control of the screen pointer provided by a GUI as associated with operating systems, such as versions of the Microsoft Windows® operating system. Embodiments are not limited to any particular pointing or tactile input device 920. Such pointing devices 920 include mice, touch pads, trackballs, remote controls and point sticks. Other input devices (not shown) can include a microphone, joystick, game pad, satellite dish, scanner, or the like.

In some embodiments, the computer 902 is operatively coupled to a display device 922 via the system bus 912. The display device 922 permits the display of information, including computer, video and other information, for viewing by a user of the computer 902. Embodiments are not limited to any particular display device 922, which may include cathode ray tube (CRT) displays (monitors), as well as flat panel displays such as liquid crystal displays (LCD's). In addition to a monitor 922, computers 902 typically include other peripheral input/output devices such as printers (not shown). Speakers 924 and 926 may provide audio output signals, responsive to commands delivered through the system bus 912.

The computer 902 also includes an operating system (not shown) that is stored on the computer-accessible media RAM 906, ROM 908, and mass storage device 910, that is accessed and executed by the processor 904. Examples of operating systems include the Microsoft Windows®, Apple MacOS®, Linux® and UNIX® operating systems. Examples are not limited to any particular operating system, however, and the construction and use of such operating systems are well known within the art.

Embodiments of the computer 902 are not limited to any type of computer 902. In varying embodiments, the computer 902 comprises a PC-compatible computer, a MacOS® operating system compatible computer, a Linux® operating system compatible computer, or a UNIX® operating system compatible computer. The construction and operation of such computers are well known within the art.

The computer 902 can be operated using at least one operating system to provide a GUI displaying icons or other indicia of functionality accessible to a user via tools such as a user-controllable pointer. The computer 902 can have at least one web browser application program executing within at least one operating system, to permit users of the computer 902 to access an intranet, extranet or Internet 914 worldwide-web pages as addressed by Universal Resource Locator (URL) addresses. Examples include the Netscape Navigator® and the Microsoft Internet Explorer® browser programs.

The computer 902 can operate in a networked environment using logical connections to one or more remote computers, such as a remote computer 928. These logical connections are achieved by a communication device coupled to, or forming a part of, the computer 902. Embodiments are not limited to a particular type of communications device. The remote computer 928 can be another computer, a server, a router, a network PC, a client, a peer device or other common network node. The logical connections depicted in FIG. 9 include a local-area network (LAN) 30 and a wide-area network (WAN) 932. Such networking environments are commonplace in offices, enterprise-wide computer networks, intranets, extranets and the Internet 914.

When used in a LAN-networking environment, the computer 902 and remote computer 928 are connected to the local network 930 through network interfaces or adapters 934, which is one type of communications device 916. The remote computer 928 also includes a network device 936. When used in a conventional WAN-networking environment, the computer 902 and remote computer 928 communicate with a WAN 932 through one or more modems (not shown). The modem, which can be internal or external, is connected to the system bus 912. In a networked environment, program modules depicted relative to the computer 902, or portions thereof, can be stored in the remote computer 928.

The computer 902 also includes a power supply 938. Each power supply 938 can be a battery, as noted above. The computer 902 also may include a removable memory storage port 956 capable of accepting a removable data storage device 958, like removable data storage device 158 of FIG. 1, provides capability for revision of machine-readable instructions, among other things. Computer-readable instructions and/or data may also be supplied to the computer 920 via coupling to a suitably-programmed removable data storage device 958 and/or via a carrier wave including modulation of computer-readable information coupled from external sources, such as the Internet 914 or other external interconnections.

The computer 902 may function as one or more of the control segments of module 120 (FIG. 1), the computer 130, the operator console 140 and/or the data acquisition and conditioning module 160, for example, via implementation of the processes 400 and 500 of FIGS. 4 and 5 as computer program modules.

Apparatus

A nondestructive imaging system 900 includes conditioning signals 134' that are exchanged between the display-and-control module 135, the at least one operator console 140 and a processor 902 via a signal conditioning module 160 that is inserted between the display-and-control module 135 and other elements of the imaging system. The conditioning includes coordinating values 904 or 906 that are selected via either the display-and-control module 135 or the operator console 140 with analogous values 908 associated with other system elements 910. The coordinated values 912 are stored in a memory 914. The stored coordinated values 912 are linked to an image 914 formed with the imaging system using at least some of the coordinated values 912 as control parameters.

Process

FIG. 10 shows a flowchart of a process 1000. Process 100 includes linking 1002 stored coordinated values to an image, the image being formed with the imaging system using at least some of the coordinated values as control parameters.

VI. Conclusion

A computer-based medical imaging system is described. Although specific embodiments have been illustrated and described herein, it will be appreciated by those of ordinary skill in the art that any arrangement which is calculated to achieve the same purpose may be substituted for the specific embodiments shown. This disclosure is intended to cover any adaptations or variations. For example, although described in procedural terms, one of ordinary skill in the art will appreciate that implementations can be made in a procedural design environment or any other design environment that provides the required relationships.

In particular, one of skill in the art will readily appreciate that the names or labels of the processes and apparatus are not intended to limit embodiments. Furthermore, additional processes and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. The terminology used in this disclosure is meant to include all object-oriented, database and communication environments and alternate technologies which provide the same functionality as described herein.

What is claimed is:

1. A process comprising:
    exchanging conditioning signals between a display-and-control module, at least one operator console and a processor, the conditioning signals being conditioned by a signal conditioning module, wherein the conditioning includes coordinating values selected via at least one of the display-and-control module with analogous values and wherein the conditioning further includes expanding a range of control functions represented via serial signals, by taking into account changing user and regulatory needs, wherein the display-and-control module, the at least one operator console and the processor are all operably coupled through a single bus; and
    storing the coordinated values in a memory, the stored coordinated values being linked to an image formed using at least some of the coordinated values as control parameters.

2. The process of claim 1 wherein the signal conditioning module includes one or more processors coupled to a non-volatile memory having instructions to cause the one or more processors to carry out a process further comprising conditioning signals in conformance with a digital X-ray radiation detector.

3. The process of claim 1 wherein coordinated values comprise at least one of peak kiloVolts, milliAmperes, milliAmpere-seconds, X-ray radiation exposure parameters.

4. A non-transitory computer-accessible medium having computer executable instructions to expand information exchange capabilities of an X-ray radiation system, the executable instructions capable of directing one or more processors to:
    modify signal exchange capabilities of a signal conditioning module in the X-ray radiation system responsive to revision of one or more elements in the X-ray radiation system, the signal conditioning module being coupled between at least one display-and-control module in the X-ray radiation system, at least one operator console and at least one system controller through a single bus, wherein the modifying includes expanding a range of control functions represented via serial signals, by taking into account changing user and regulatory needs; and
    coordinate values selected via the display-and-control module, the operator console and the system controller with analogous values in at least one other of the display-and-control module, the operator console and the system controller, wherein coordinated values are linked to an image formed with the X-ray radiation system using at least some of the coordinated values as control parameters.

5. The non-transitory computer-accessible medium of claim 4, wherein the computer-accessible medium comprises a detachable computer-accessible medium.

6. The non-transitory computer-accessible medium of claim 4, wherein the computer-accessible medium comprises a nonvolatile memory associated with the signal conditioning module.

7. The non-transitory computer-accessible medium of claim 4, wherein the executable instructions cause the one or more processors to modify signal exchange capabilities in conformance with a range of signal exchange capabilities that is expanded in comparison to design criteria for the X-ray radiation system.

8. The non-transitory computer-accessible medium of claim 4, wherein the executable instructions cause the one or more processors to modify signal exchange capabilities to facilitate operation of a digital X-ray radiation detection system.

9. The non-transitory computer-accessible medium of claim 4, wherein the computer-accessible medium is configured to store revised executable instructions supplied from a remote data source.

10. An apparatus to expand the information exchange capabilities of a medical imaging system with an operator interface and at least one memory, the apparatus comprising:
    a processor to execute instructions to configure the operator interface and a control system in the medical imaging system by:
    supplying coordinated information to multiple display elements on the operator interface to synchronize information displayed by each of the multiple display elements;
    supplying coordinating data internal to the control system at the medical imaging system to synchronize internal data with the information displayed by each of the multiple elements;
    supplying coordination descriptions of a nondestructive imaging task to the at least one memory, including an image and data of that image; and
    a signal conditioning module coupled to the processor through a single bus and coupled to the control system and configured for insertion into the medical imaging system, wherein the signal conditioning module receives at least imaging data from the medical imaging system and expands a range of control functions represented via serial signals, by taking into account changing user and regulatory needs.

11. The apparatus of claim 10, further comprising a nonvolatile memory having instructions to cause the processor to configure one of the multiple display elements to display one or more graphical user interfaces.

12. The apparatus of claim 11, wherein the nonvolatile memory is configured to accept one or more imaging system modifications so as to cause the processor to configure the operator interface and control system.

13. The apparatus of claim 12, wherein the one or more graphical user interfaces display information that is at least descriptive of imaging system capabilities.

14. The apparatus of claim 10, wherein the processor includes serial data exchange capability and parallel data exchange capability, and wherein the processor provides augmented capability reflective of imaging system modifications for data exchange via serial data exchange.

15. The apparatus of claim 14, wherein the imaging system modifications include a digital X-ray radiation detection system.

16. The apparatus of claim 10, wherein the processor communicates imaging system modifications through a serial data exchange.

* * * * *